(12) United States Patent
Horiuchi et al.

(10) Patent No.: US 10,874,363 B2
(45) Date of Patent: Dec. 29, 2020

(54) RADIATION DETECTION DEVICE

(71) Applicant: FUJIFILM Corporation, Tokyo (JP)

(72) Inventors: Hisatsugu Horiuchi, Kanagawa (JP);
Masateru Tateishi, Kanagawa (JP);
Shinsuke Noguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/568,864

(22) Filed: Sep. 12, 2019

(65) Prior Publication Data

US 2020/0100739 A1   Apr. 2, 2020

(30) Foreign Application Priority Data

Sep. 28, 2018  (JP) ................. 2018-184311

(51) Int. Cl.
*G01T 1/24* (2006.01)
*A61B 6/00* (2006.01)
*G01T 1/20* (2006.01)
*G03B 42/04* (2006.01)

(52) U.S. Cl.
CPC .............. *A61B 6/4405* (2013.01); *G01T 1/20* (2013.01); *G03B 42/04* (2013.01)

(58) Field of Classification Search
CPC ....... G01T 1/20; G01T 1/20188; G03B 42/04; G03B 42/042
See application file for complete search history.

(56) References Cited

U.S. PATENT DOCUMENTS

2019/0018151 A1* 1/2019 Kawaguchi .............. A61B 6/00

FOREIGN PATENT DOCUMENTS

JP      2012-63341 A    3/2012

* cited by examiner

*Primary Examiner* — Don K Wong
(74) *Attorney, Agent, or Firm* — Birch, Stewart, Kolasch & Birch, LLP.

(57) ABSTRACT

There is provided a radiation detection device capable of protecting a radiation detection panel stored thereinside. A radiation detection device includes: a front surface member; a rear surface member that is assembled with the front surface member and that comprises an outer rib formed along an outer edge and an inner rib formed along the outer rib inside the outer rib; and a radiation detection panel that is disposed between the front surface member and the rear surface member and detects radiation incident from the front surface member side.

13 Claims, 13 Drawing Sheets

RADIATION DETECTION DEVICE

CROSS-REFERENCE TO RELATED APPLICATION

This application claims priority under 35 USC 119 from Japanese Patent Application No. 2018-184311 filed Sep. 28, 2018, the disclosure of which is incorporated by reference herein.

BACKGROUND

Technical Field

The present invention relates to a radiation detection device.

Related Art

JP2012-063341A discloses a structure of a portable radiation image detection device. In the portable radiation image detection device, a flat panel detector (FPD) formed by laminating a charge generation layer, which absorbs X-rays and converts the X-rays into electric charges, on a thin film transistor (TFT) active matrix substrate is stored inside a housing with an approximately rectangular planar shape. In addition, a circuit board is disposed on the rear surface side of the FPD.

SUMMARY

The portable radiation image detection device disclosed in JP2012-063341A may be attached to the imaging table in the imaging room, or may be taken out of the imaging room and inserted between the bed in the patient's room and the patient. Thus, the portable radiation image detection device is used in various forms. For this reason, compared with a non-portable radiation image detection device, there is a possibility that a local impact may be applied due to an unexpected drop or the like. Since a radiation detection panel is stored inside the portable radiation image detection device, it is preferable to appropriately protect the radiation detection panel.

Therefore, it is an object of the invention to provide a radiation detection device capable of protecting a radiation detection panel stored thereinside.

In order to achieve the aforementioned object, a radiation detection device according to the invention comprises: a front surface member; a rear surface member that is assembled with the front surface member and that comprises an outer rib formed along an outer edge and an inner rib formed along the outer rib inside the outer rib; and a radiation detection panel that is disposed between the front surface member and the rear surface member and detects radiation incident from the front surface member side.

In the radiation detection device according to the invention, the outer rib and the inner rib are formed in a frame shape.

In the radiation detection device according to the invention, the outer rib has a portion formed thicker than the inner rib.

In the radiation detection device according to the invention, the outer rib and the inner rib are connected to each other by a connection rib.

In the radiation detection device according to the invention, at least a part of the connection rib is a corner portion connection rib extending from a corner portion of the outer rib to the inner rib, and the inner rib is disposed perpendicular to the corner portion connection rib.

In the radiation detection device according to the invention, the outer rib, the inner rib, and the connection rib form a truss structure.

The radiation detection device according to the invention further comprises a support plate that supports the radiation detection panel, and the support plate is bonded to the rear surface member.

In the radiation detection device according to the invention, the support plate is bonded to a corner portion of the rear surface member.

In the radiation detection device according to the invention, a reinforcing rib is formed on the support plate, and the reinforcing rib and the rear surface member are bonded to each other.

In the radiation detection device according to the invention, an opening portion through which an externally inserted member is inserted is formed on side surfaces of the outer rib and the inner rib, and an opening connection rib is formed at both ends of the opening portion.

In the radiation detection device according to the invention, the opening portion is formed in a central portion of the rear surface member.

In the radiation detection device according to the invention, the opening portion is formed on two sides adjacent to each other in the rear surface member.

In the radiation detection device according to the invention, a protection rib surrounding the externally inserted member inserted through the opening portion is formed on the support plate.

In the radiation detection device according to the invention, the radiation detection panel is disposed between the front surface member and the rear surface member. In the rear surface member, the outer rib is formed along the outer edge, and the inner rib is formed inside the outer rib. Therefore, the stiffness of the rear surface member is higher than that in a structure that does not have either the inner rib or the outer rib or a structure that does not have any of the inner rib and the outer rib. For this reason, for example, even in a case where an impact at the time of drop is applied to the radiation detection device, the rear surface member is hardly deformed. Accordingly, the radiation detection panel is protected.

BRIEF DESCRIPTION OF THE DRAWINGS

Exemplary Embodiments of the present invention will be described in detail with reference to the following figures, wherein.

DETAILED DESCRIPTION

Radiation Detection Device

Figure 1:
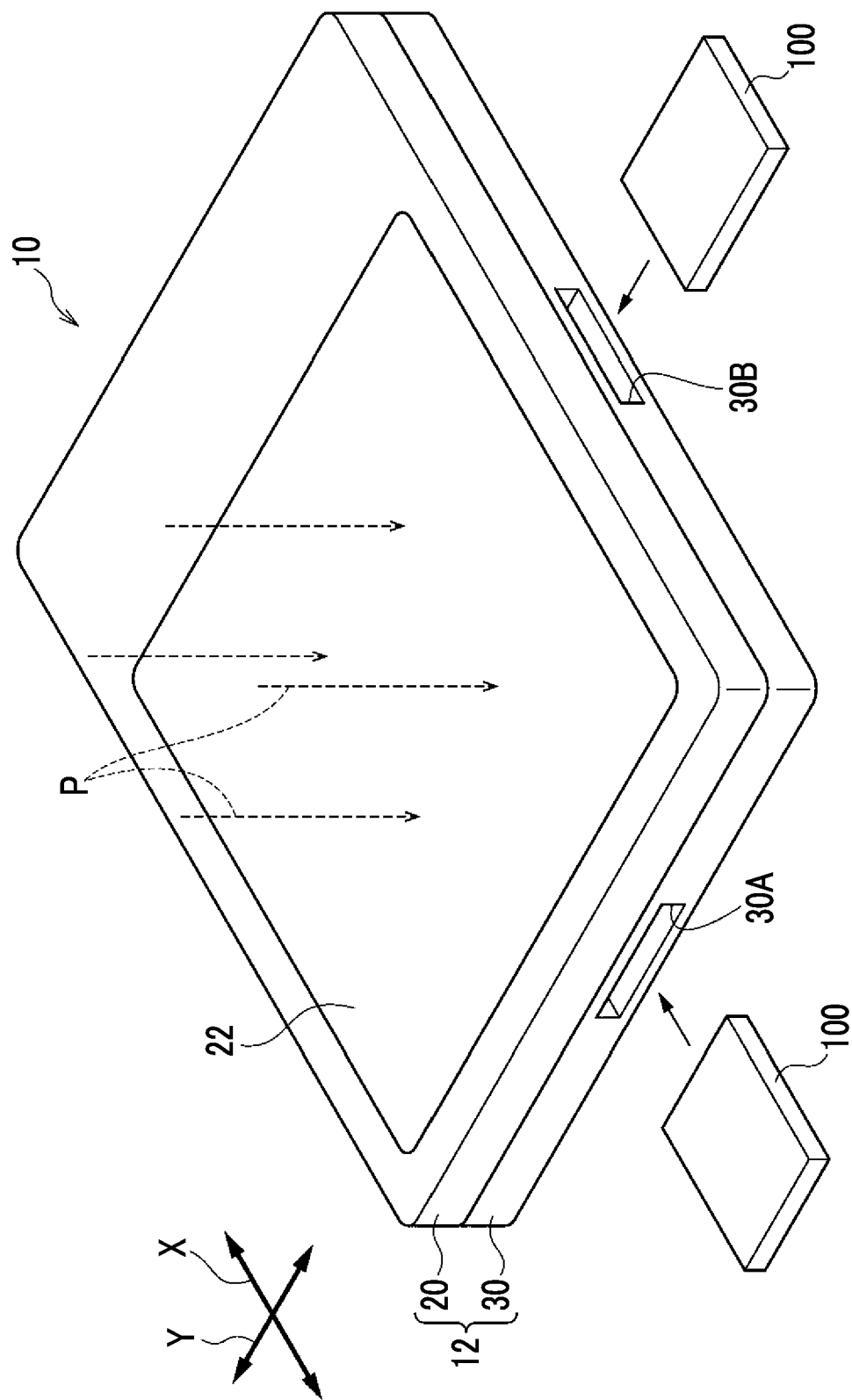
FIG. 1 is a perspective view showing a radiation detection device according to the present embodiment.

FIG. 1 is a schematic perspective view of a radiation detection device 10 according to an embodiment of the invention. The radiation detection device 10 is an electronic cassette having an approximately rectangular shape in a plan view, and is driven by a battery 100 mounted on a housing 12 configured to include a front surface member 20 and a rear surface member 30.

The planar size of the housing 12 is, for example, a size according to the international standard ISO4090: 2001 similar to a half size (383.5 mm×459.5 mm) film cassette or imaging plate (IP) cassette. Therefore, the radiation detection device 10 can also be used in a state in which the radiation detection device 10 is attached to an imaging table for a film cassette or an IP cassette.

The battery 100 is mounted on the radiation detection device 10 by being inserted into opening portions 30A and 30B formed at the central portions of two adjacent sides of the rear surface member 30 having an approximately rectangular shape in a plan view. The radiation detection device 10 is driven in a state in which the battery 100 is mounted in at least one of the opening portions 30A and 30B.

The opening portion 30A is an opening portion formed at the central portion of a side surface (short side) along the Y direction shown in FIG. 1 in the radiation detection device 10, and the opening portion 30B is an opening portion formed at the central portion of a side surface (long side), which is adjacent to the side surface on which the opening portion 30A is formed and extends along the X direction perpendicular to the Y direction.

The front surface member 20 attached to the rear surface member 30 is configured to include an approximately rectangular transmission plate 22. The transmission plate 22 is formed of, for example, a carbon material having a high X-ray transmittance. Radiation (X-rays P in the present embodiment) is incident from a direction approximately perpendicular to the in-plane direction of the transmission plate.

The front surface member 20 and the rear surface member 30 are formed by die casting using a magnesium alloy (Mg alloy) in the present embodiment. However, the material and manufacturing method of the front surface member 20 and the rear surface member 30 are not limited thereto, and the front surface member 20 and the rear surface member 30 can be molded using various metals, resins, and the like.

Figure 2:
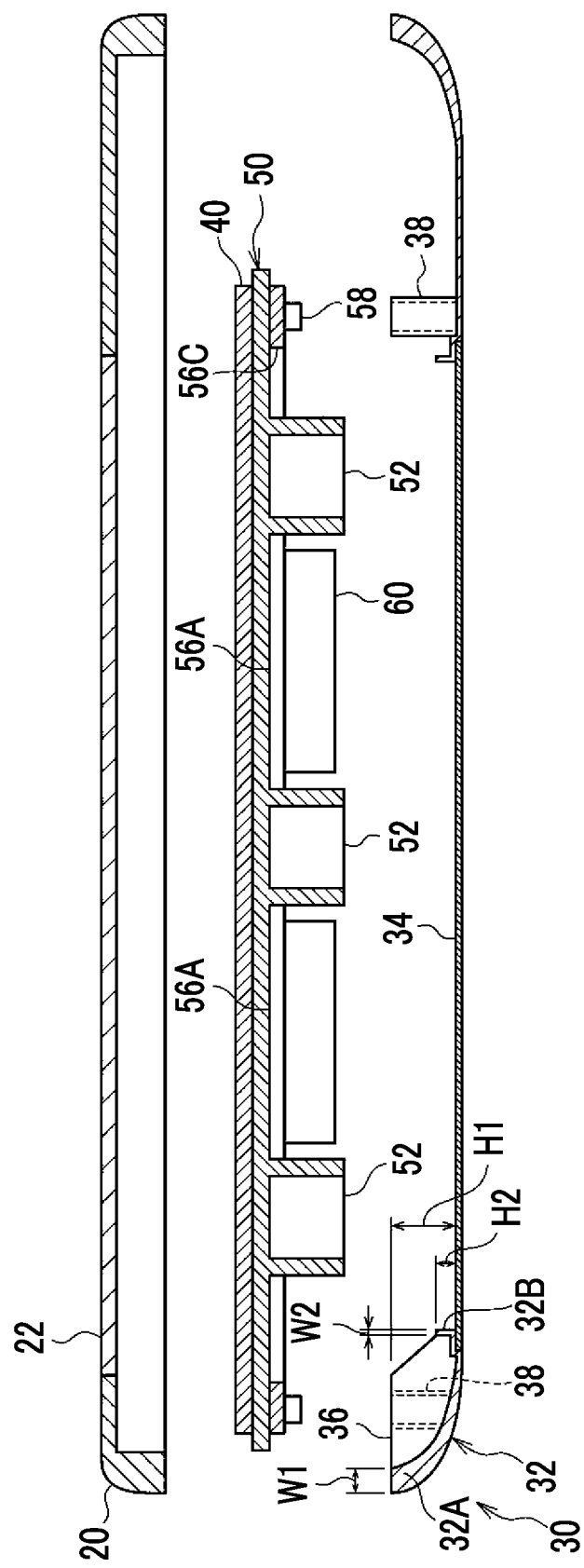
FIG. 2 is an exploded side sectional view showing a state in which the radiation detection device according to the present embodiment is disassembled.
Figure 3:
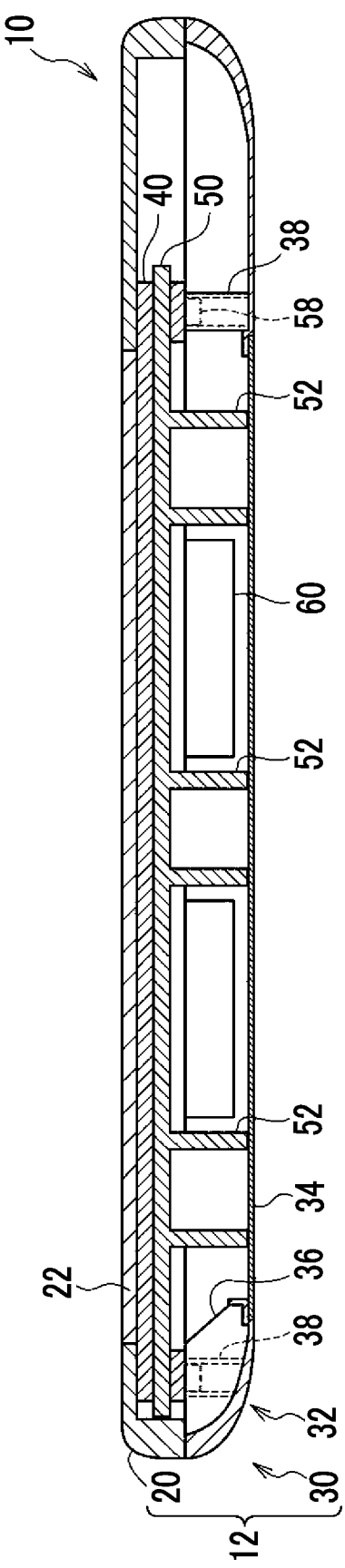
FIG. 3 is a side sectional view showing the radiation detection device according to the present embodiment.

FIG. 2 is an exploded cross-sectional view of the housing 12 (refer to FIGS. 1 and 3). As shown in FIG. 2, a radiation detection panel 40, a support plate 50 to which the radiation detection panel 40 is attached, and a control substrate 60 for controlling the radiation detection panel 40 are provided inside the housing 12 so as to be interposed between the front surface member 20 and the rear surface member 30.

The radiation detection device 10 shown in FIG. 3 is formed by assembling the front surface member 20, the rear surface member 30, the radiation detection panel 40, the support plate 50, the control substrate 60, the battery 100, and the like (refer to FIG. 1).

In FIGS. 2 and 3, the configuration of the support plate 50 is shown in a simplified manner. That is, the support plate 50 shown in FIGS. 2 and 3 schematically shows the configuration of the support plate 50 in which a support post 54, a reinforcing rib 56B, and a protection rib 56D to be described later are omitted.

Back Member-Double Frame

Figure 4:
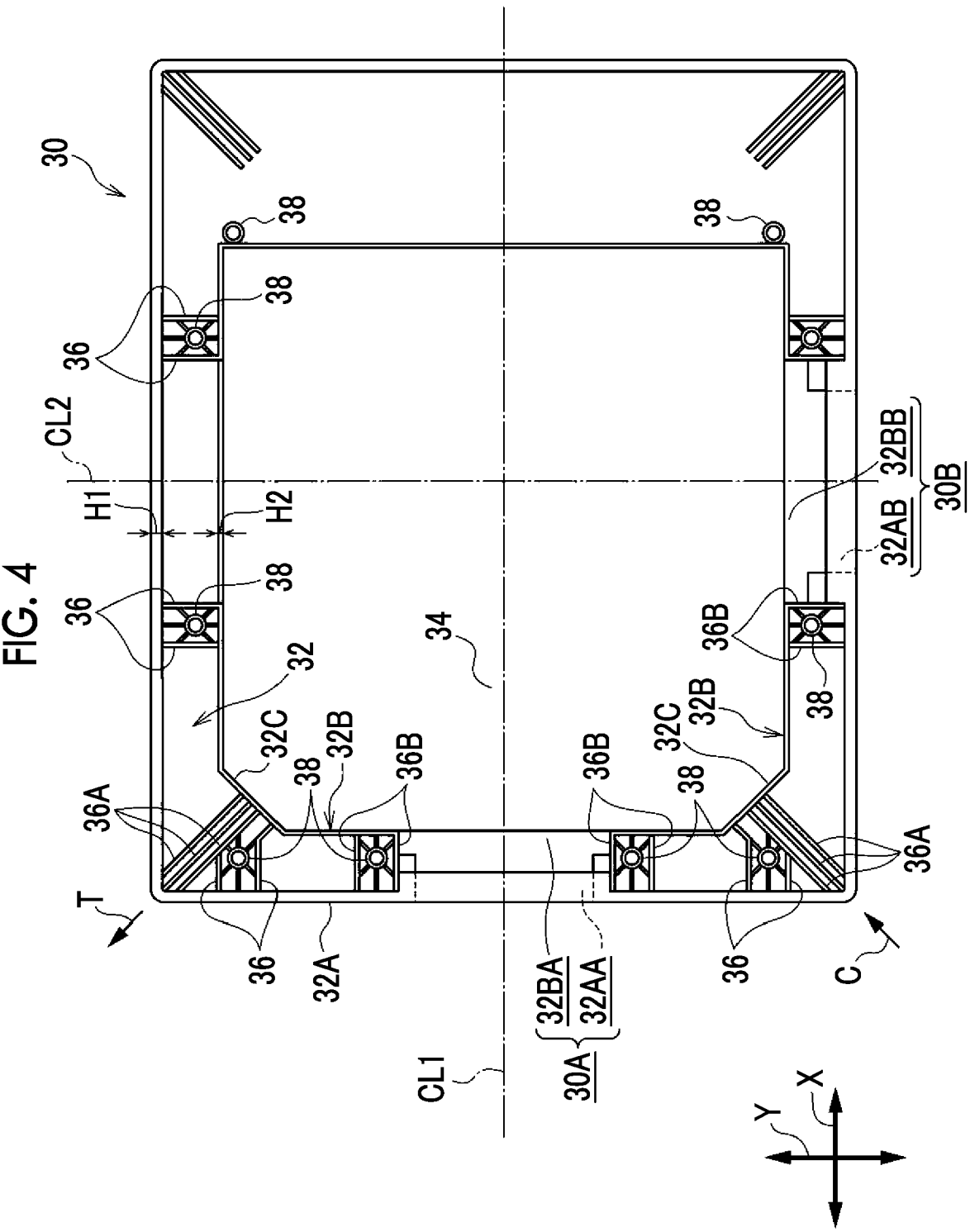
FIG. 4 is a front view showing a rear surface member in the radiation detection device according to the present embodiment.

The rear surface member 30 is formed to comprise a double frame 32 (an outer rib 32A and an inner rib 32B) and a bottom plate 34. As shown in FIG. 4, the double frame 32 is formed in a rectangular frame shape along the X and Y directions described above, and as shown in FIG. 2, the bottom plate 34 is fitted onto the bottom surface. The bottom plate 34 is fixed to the double frame 32 using a screw or the like.

In the double frame 32, the inner rib 32B for reinforcing a rectangular opening end into which the bottom plate 34 is fitted is erected toward the front surface member 20. The double frame 32 is gradually raised from the bottom surface onto which the bottom plate 34 is fitted to the outer edge portion in a direction of the front surface member 20, and the raised portion is the outer rib 32A.

The rising height H1 of the outer rib 32A is set to be larger than the rising height H2 of the inner rib 32B, and the thickness W1 of the outer rib 32A is set to be larger than the thickness W2 of the inner rib 32B. As an example, the thickness W1 is about 4 mm to 5 mm, and the thickness W2 is about 0.8 mm. In the present embodiment, the outer rib 32A is formed to be thicker than the inner rib 32B over the entire circumference. However, the embodiment of the invention is not limited thereto, and the outer rib 32A may be formed partially thinner than the inner rib 32B. In other words, the inner rib 32B may be formed partially thicker than the outer rib 32A.

A packing (not shown) formed of resin is disposed between the front surface member 20 and the surface of the outer rib 32A, which faces the front surface member 20, in the rear surface member 30 and is compressed between the front surface member 20 and the rear surface member 30, so that the internal space formed between the front surface member 20 and the rear surface member 30 is a watertight space.

FIG. 4 shows a plan view of the rear surface member 30 (a state in which the rear surface member 30 is viewed from the incidence direction of an X-ray P shown in FIG. 1). As shown in FIG. 4, the outer rib 32A is formed along the outer edge of the rear surface member 30 in a frame shape in which each side extends along the X and Y directions. On the inner side of the outer rib 32A, the inner rib 32B is formed in a frame shape along the outer rib 32A.

It is assumed that "along" in the invention includes not only a state in which the outer rib 32A and the inner rib 32B are disposed in parallel so as to be spaced apart from each other but also a state in which the outer rib 32A and the inner rib 32B are disposed in parallel so as to be in contact with each other. In addition, the outer rib 32A and the inner rib 32B do not need to be strictly parallel, and a case where there is twisting due to manufacturing variations or a state in which at least one of the outer rib 32A or the inner rib 32B is disposed in a zigzag or wave shape is also included.

The "frame shape" in the invention indicates a state in which the outer rib 32A is disposed in a portion, which covers the length of half or more of the circumferential length, in the outer edge portion of the rear surface member 30. The outer rib 32A does not need to be continuous, and may have an intermittent portion. In addition, as will be described later, an opening portion by a through hole may be formed in the outer rib 32A. The same applies to the inner rib 32B.

Through holes 32AA and 32AB are formed in the outer rib 32A, so that the battery 100 (refer to FIG. 1) can be inserted thereinto. The inner rib 32B is not formed on the inner side in the insertion direction of the battery 100 in the through holes 32AA and 32AB. In other words, in the inner rib 32B, intermittent portions 32BA and 32BB are formed on the inner sides of the through holes 32AA and 32AB in the outer rib 32A.

The opening portion 30A is formed by the through hole 32AA and intermittent portion 32BA, and the opening portion 30B is formed by the through hole 32AB and intermittent portion 32BB. The through holes 32AA and 32AB and the intermittent portions 32BA and 32BB are examples of the "opening portion" in the invention.

Back Member-Connection Rib

As shown in FIG. 4, a plurality of connection ribs 36 are bonded to the outer rib 32A and the inner rib 32B, and the outer rib 32A and the inner rib 32B are connected to each other by the connection ribs 36. The connection rib 36 extends in a direction approximately perpendicular to the outer rib 32A and the inner rib 32B. In the following description, the connection rib 36 extending from the corner portion of the outer rib 32A toward the inner rib 32B is referred to as a corner portion connection rib 36A. In addition, the connection ribs 36 formed at both ends of the opening portions 30A and 30B are referred to as opening connection ribs 36B.

The "corner portion" of the outer rib 32A refers to a portion that is closer to the outer rib 32A along the X direction than a center line CL1 along the X direction of the rear surface member 30 and closer to the outer rib 32A along the Y direction than a center line CL2 along the Y direction of the rear surface member 30. In addition, the "central portion" of the outer rib 32A refers to a portion other than the "corner portion" described above, which is a portion including the center lines CL1 and CL2.

A plurality of corner portion connection ribs 36A are formed for each corner portion, and extend from the corner portion of the outer rib 32A toward the inner rib 32B in a direction crossing the X and Y directions. In the inner rib 32B, an oblique portion 32C extending in a direction approximately perpendicular to the corner portion connection rib 36A is formed in a portion facing the corner portion of the outer rib 32A. In other words, the inner rib 32B is formed in a frame shape in which a part of the rectangular corner portion is chamfered, and the oblique portion 32C connected such that the corner portion connection rib 36A is perpendicular thereto is formed in the chamfered portion.

The oblique portion 32C is formed in an end portion of a side, which is a side along the short side of the radiation detection device 10 (that is, a side along the Y direction) and on which the opening portion 30A is formed, among the sides of the inner rib 32B.

On the other hand, a side, which is a side along the short side of the radiation detection device 10 (that is, a side along the Y direction) and on which the opening portion 30A is not formed, among the sides of the inner rib 32B is disposed such that the separation distance from the outer rib 32A is larger than those of the other sides.

The opening connection rib 36B connects the outer rib 32A and the inner rib 32B at both end portions of the intermittent portions 32BA and 32BB in the inner rib 32B. A mounting rib 38 that forms a mounting hole for fixing the support plate 50 (refer to FIG. 2) is connected to the opening connection rib 36B.

A plurality of mounting ribs 38 are provided, and are also connected to the connection rib 36 disposed in the vicinity of the corner portion connection rib 36A in addition to the opening connection rib 36B. The mounting rib 38 is also connected to the side of the inner rib 32B where the separation distance from the outer rib 32A is larger than those of the other sides. In addition, "vicinity of the corner portion connection rib 36A" refers to a portion included in the "corner portion" described above.

Support Plate

Figure 5:
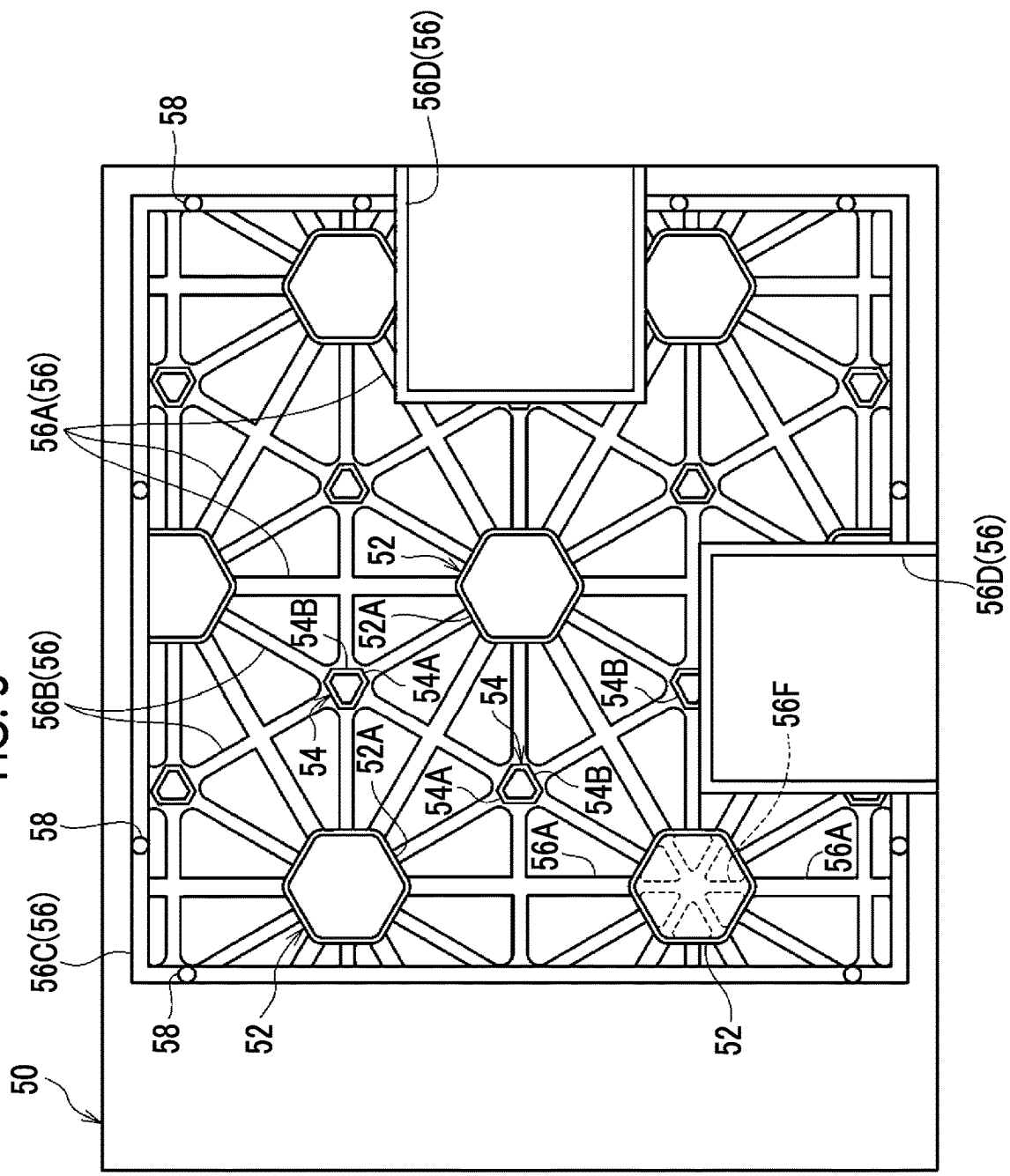
FIG. 5 is a front view showing a support plate in the radiation detection device according to the present embodiment.

FIG. 5 shows a plan view of the support plate 50 (a state in which the support plate 50 is viewed from a direction opposite to the incidence direction of the X-ray P shown in FIG. 1). That is, a surface opposite to the surface to which the radiation detection panel 40 shown in FIG. 2 is attached is shown.

The support plate 50 is formed using a magnesium lithium alloy (MgLi alloy) in which the mixing ratio (mass percentage) of lithium (Li) to magnesium (Mg) is 9%.

The mixing ratio of lithium (Li) is not limited to 9%, and may be 1.5% or more and 14% or less. In a case where the mixing ratio is less than 1.5%, it is difficult to obtain the weight reduction effect. That is, between a MgLi alloy and a Mg alloy having the same stiffness, the weight of the Mg alloy can be reduced. In a case where the mixing ratio is larger than 14%, it is necessary to consider corrosion resistance.

A support post 52 is formed integrally with the support plate 50, and as shown in FIG. 2, is formed in a tubular shape having an axial direction along the out-of-plane direction (a direction perpendicular to the in-plane direction, that is, a normal direction) of the support plate 50. The wall surface of the support post 52 is formed perpendicular to the support plate 50.

As shown in FIG. 3, in a state in which the housing 12, the radiation detection panel 40, and the support plate 50 are assembled, the transmission plate 22 is disposed in contact with the radiation detection panel 40. In addition, the support post 52 and the support post 54 to be described later are disposed in contact with the bottom plate 34 in the rear surface member 30. "Disposed in contact" includes a state in which there is a gap that allows the support posts 52 and 54 to be in contact with the bottom plate 34 in a case where the transmission plate 22 is pressed from the outside at the time of use of the radiation detection device 10. Although described in detail later, a case where the support post and the bottom plate are integrally formed is included.

As shown in FIG. 5, the support posts 52 are formed in an approximately regular hexagonal shape, and are disposed at predetermined intervals in a plan view. More specifically, the center of the support post 52 is disposed on the grid point of the equilateral triangle grid filling the plane. Each apex in the hexagonal support post 52 is chamfered in a curvilinear shape and disposed on the side of a triangle forming the equilateral triangle grid.

Between the support posts 52, the hexagonal support post 54 in which adjacent sides have different lengths is disposed. More specifically, the center of the support post 54 is disposed on the center of gravity of the triangle forming the above-described equilateral triangle grid. In the support post 54, a short side 54A and a long side 54B are formed so as to be alternately adjacent to each other, the short side 54A faces a side 52A of the support post 52, and the long side 54B faces the long side 54B of the adjacent support post 54.

In addition, between the support posts 52 adjacent to each other, the reinforcing rib 56A is formed along the equilateral triangle grid described above. In addition, the reinforcing rib 56B is formed between the support post 52 and the support post 54 adjacent to each other and between the support posts 54 adjacent to each other.

Furthermore, a frame-shaped outer peripheral portion reinforcing rib 56C is formed along the outer periphery of the support plate 50 so as to surround the support posts 52 and 54 and the reinforcing ribs 56A and 56B. A protruding portion 58 is formed in the outer peripheral portion reinforcing rib 56C that is an example of a reinforcing rib in the invention. The protruding portion 58 is formed at a position corresponding to the mounting hole formed by the mounting rib 38 of the rear surface member 30 described above. By inserting the protruding portion 58 into the mounting hole and bonding these to each other, the rear surface member 30 and the support plate 50 are bonded to each other. The mounting rib 38 is connected to the connection rib 36 disposed in the vicinity of the opening connection rib 36B and the corner portion connection rib 36A in the rear surface member 30. Therefore, the outer peripheral portion reinforcing rib 56C of the support plate 50 is bonded to the rear surface member 30 at the corner portions of the rear surface member 30 and both end portions of the opening portions 30A and 30B.

Furthermore, the protection rib 56D is formed at positions corresponding to the opening portions 30A and 30B in the rear surface member 30. The protection rib 56D divides the outer peripheral portion reinforcing rib 56C, and is disposed so as to surround the battery 100 (refer to FIG. 1) inserted into the opening portions 30A and 30B.

Radiation Detection Panel

Figure 6:
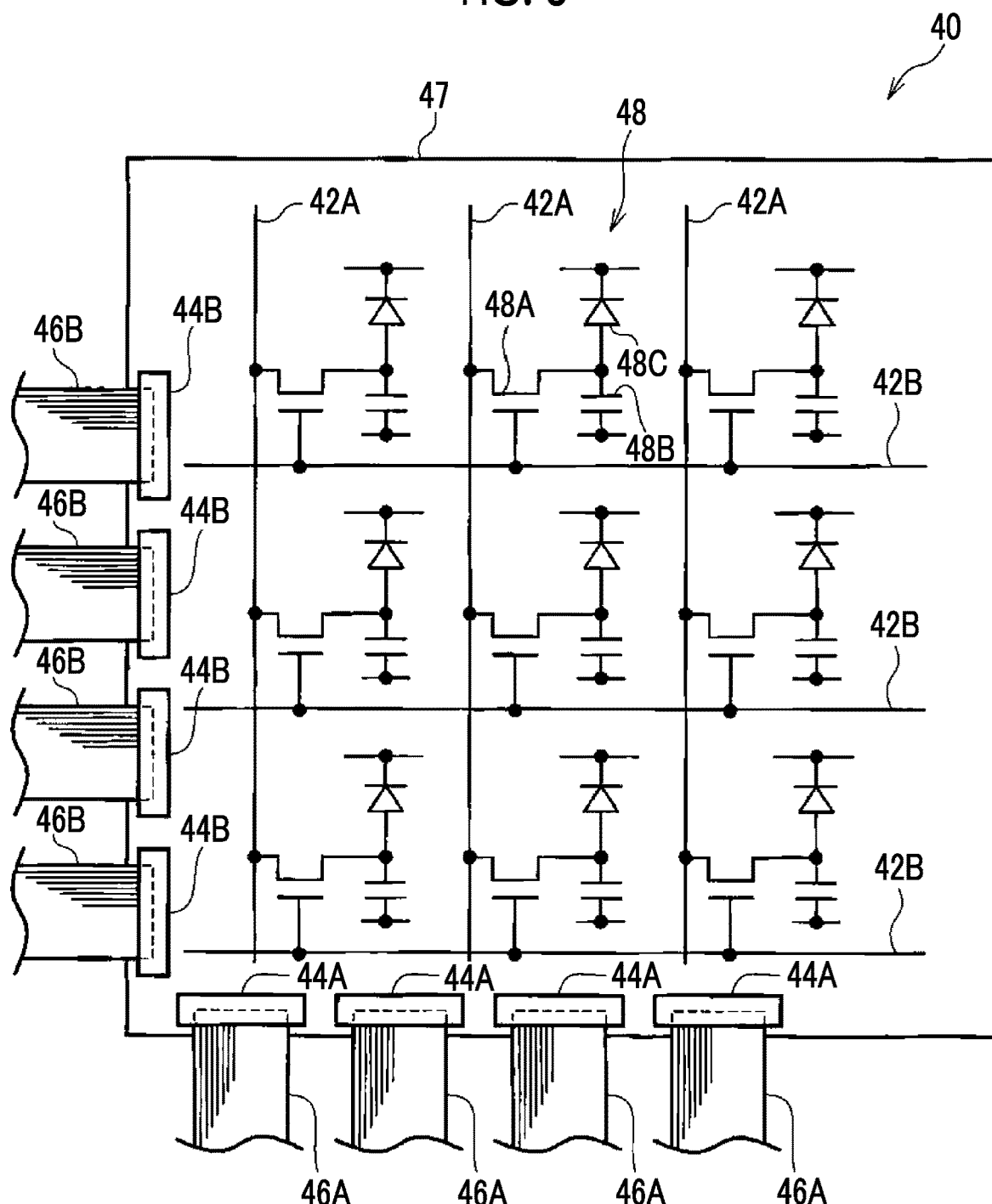
FIG. 6 is a front view showing a radiation detection panel in the radiation detection device according to the present embodiment.

The radiation detection panel 40 is a quadrilateral flat plate having four sides at the outer edge in a plan view. As shown in FIG. 6, the radiation detection panel 40 includes a TFT active matrix substrate (TFT substrate) 47 in which a thin film transistor 48A and a capacitor 48B are formed on an insulating substrate. On the TFT substrate 47, a scintillator (not shown) for converting incident X-rays into light is disposed. On the TFT substrate 47, a sensor unit 48C that generates electric charges by incidence of light converted by the scintillator is formed.

On the TFT substrate 47, a plurality of pixels 48 each including the sensor unit 48C, the capacitor 48B, and the thin film transistor 48A are provided in a two-dimensional manner in a predetermined direction (horizontal direction in FIG. 6=row direction) and a direction (vertical direction in FIG. 6=column direction) crossing the predetermined direction.

A plurality of gate lines 42B for turning on and off each thin film transistor 48A and a plurality of data lines 42A for reading out electric charges through the thin film transistor 48A in the ON state are provided in the radiation detection panel 40. The gate lines 42B and the data lines 42A extend in a direction crossing each other.

A plurality of connectors 44A for line connection are provided side by side on one end side of the data line 42A, and a plurality of connectors 44B are provided side by side on one end side of the gate line 42B.

One end of a flexible cable 46A is connected to the connector 44A, and one end of the flexible cable 46B is connected to the connector 44B.

Control Substrate

Figure 7:
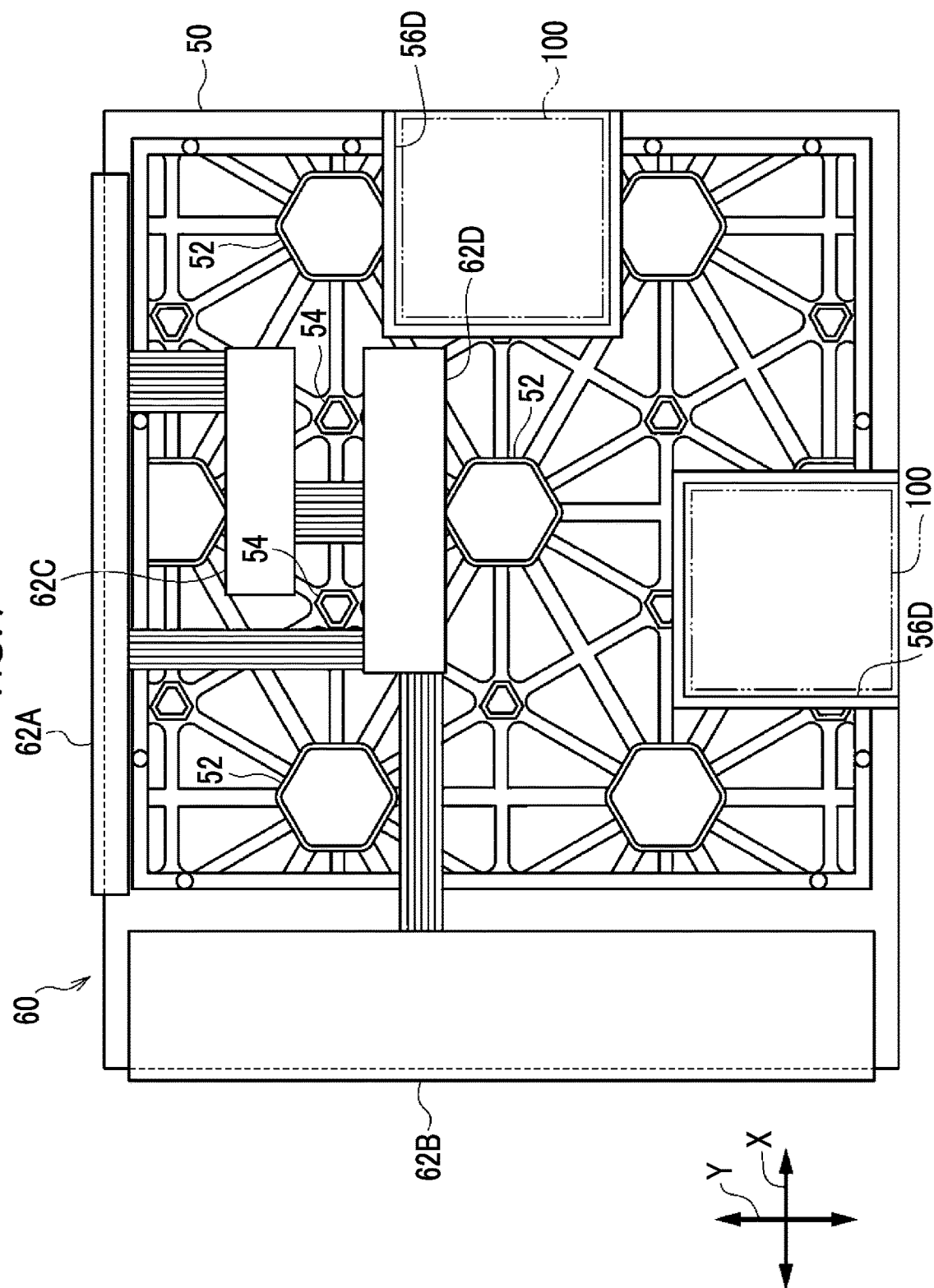
FIG. 7 is a front view showing a control substrate in the radiation detection device according to the present embodiment.

As shown in FIG. 7, a signal processing unit 62A, a gate line driver 62B, an image memory 62C, a controller 62D, a wireless communication unit (not shown), and the like are provided on the control substrate 60.

Each gate line 42B of the TFT substrate 47 is connected to the gate line driver 62B through the flexible cable 46B, and each data line 42A of the TFT substrate 47 is connected to the signal processing unit 62A through the flexible cable 46A.

The gate line driver 62B and the signal processing unit 62A are disposed along two adjacent sides of the support plate 50, and are directly bonded to the support plate 50. That is, the gate line driver 62B and the signal processing unit 62A are disposed so as to be in direct contact with the support plate 50 without using a mount member, such as a resin.

The gate line driver 62B and the signal processing unit 62A are attached to a side of the support plate 50 different from the side on which the protection rib 56D for protecting the battery 100 is provided. The image memory 62C and the controller 62D are attached at positions that do not interfere with the support posts 52 and 54.

The arrangement of the gate line driver 62B, the signal processing unit 62A, the image memory 62C, and the controller 62D shown in FIG. 7 is an example, and can be appropriately changed according to the shapes or the arrangement of the support posts. In other words, the arrangement of the support posts can be appropriately adjusted according to the sizes or the shapes of the gate line driver 62B, the signal processing unit 62A, and the image memory 62C.

The thin film transistors 48A of the TFT substrate 47 are sequentially turned on row by row by a signal supplied from the gate line driver 62B through the gate line 42B. The electric charges read out by the thin film transistor 48A that is turned on are transmitted as an electric signal through the data line 42A and input to the signal processing unit 62A. As a result, the electric charges are sequentially read out row by row, and a two-dimensional radiation image can be acquired.

Although not shown, the signal processing unit 62A includes a sample and hold circuit and an amplification circuit for amplifying the input electric signal for each data line 42A, and the electric signal transmitted through each data line 42A is amplified by the amplification circuit and then held in the sample and hold circuit. In addition, a multiplexer and an analog/digital (A/D) converter are connected in order to the output side of the sample and hold circuit. The electric signals held in the respective sample and hold circuits are sequentially (serially) input to the multiplexer and converted into digital image data by the A/D converter.

The image memory 62C is connected to the signal processing unit 62A, and the image data output from the A/D converter of the signal processing unit 62A is sequentially stored in the image memory 62C. The image memory 62C has a storage capacity capable of storing image data of a predetermined number of sheets, and image data obtained by imaging is sequentially stored in the image memory 62C each time a radiation image is captured.

The image memory 62C is connected to the controller 62D. The controller 62D is a microcomputer, and comprises a central processing unit (CPU), a memory including a read only memory (ROM) and a random access memory (RAM), and a non-volatile storage unit including a flash memory and the like. The controller 62D controls the overall operation of the radiation detection device 10.

A wireless communication unit (not shown) is connected to the controller 62D. The wireless communication unit complies with a wireless local area network (LAN) standard represented by Institute of Electrical and Electronics Engineers (IEEE) 802.11a/b/g or the like, and controls transmission of various kinds of information to and from an external apparatus by wireless communication. The controller 62D can wirelessly communicate with an external apparatus, such as a console that controls the entire radiation imaging, through the wireless communication unit, so that it is possible to transmit and receive various kinds of information to and from the console.

The various circuits or elements (the gate line driver 62B, the signal processing unit 62A, the image memory 62C, the wireless communication unit, or the microcomputer functioning as the controller 62D) operate with the power supplied from the battery 100. In FIG. 7, wirings for connecting the battery 100 to various circuits or elements are not shown.

In the radiation detection device 10 according to the embodiment of the invention, as shown in FIGS. 2 and 3, the radiation detection panel 40 is disposed between the front surface member 20 and the rear surface member 30. The outer rib 32A is formed along the outer edge of the rear surface member 30, and the inner rib 32B is formed on the inner side of the outer rib 32A. Therefore, the stiffness of the rear surface member 30 is higher than that in a structure that does not have either the inner rib 32B or the outer rib 32A or a structure that does not have any of the inner rib 32B and the outer rib 32A. For this reason, for example, even in a case where an impact at the time of drop is applied to the radiation detection device 10, the rear surface member 30 is hardly deformed. Accordingly, the radiation detection panel 40 is protected.

In the radiation detection device 10, as shown in FIG. 4, the outer rib 32A and the inner rib 32B are formed in a frame shape. For this reason, the rear surface member 30 is less likely to be distorted as compared with a case where at least one of the outer rib or the inner rib is formed, for example, only in a corner portion of the rear surface member 30 or only on a side along the X direction or the Y direction. Therefore, the effect of protecting the radiation detection panel 40 is high.

In the radiation detection device 10, the outer rib 32A is formed thicker than the inner rib 32B. Therefore, for example, compared with a case where the thickness of the inner rib is larger than that of the outer rib or a case where the inner rib and the outer rib have the same thickness, the outer rib to which the impact from the outside is directly applied is less likely to be deformed. As a result, deformation of the rear surface member 30 due to impact can be efficiently suppressed.

In the radiation detection device 10, the outer rib 32A and the inner rib 32B are connected to each other by the connection rib 36. Therefore, the impact received by the outer rib 32A can be transmitted to the inner rib 32B through the connection rib 36. As a result, compared with a configuration without the connection rib 36, the effect of improving the stiffness of the rear surface member 30 by the inner rib 32B can be enhanced.

A part of the connection rib 36 is the corner portion connection rib 36A extending from the corner portion of the outer rib 32A toward the inner rib 32B, and the oblique portion 32C in the inner rib 32B is formed so as to be perpendicular to the corner portion connection rib 36A.

Therefore, an impact C applied to the corner portion of the outer rib 32A is transmitted to the oblique portion 32C through the corner portion connection rib 36A. In this case, the corner portion connection rib 36A can function as a compression member between the outer rib 32A and the oblique portion 32C to resist an impact.

In a case where the impact C is applied to the corner portion of the outer rib 32A, a tensile force T acts on a corner portion adjacent to the corner portion to which the impact is applied. In this case, the corner portion connection rib 36A can function as a tension member between the outer rib 32A and the oblique portion 32C to suppress the deformation of the rear surface member 30.

As shown in FIGS. 2 and 3, the radiation detection device 10 comprises the support plate 50 for supporting the radiation detection panel 40, and the protruding portion 58 in the support plate 50 is inserted into the mounting hole formed by the mounting rib 38 in the rear surface member 30 and bonded thereto. Therefore, the rear surface member 30 is stiffened by the support plate 50 that is a plate material, and shear deformation along the in-plane direction of the support plate 50 is suppressed. In addition, bending deformation along the out-of-plane direction of the support plate 50 is suppressed.

The support plate 50 is bonded to the rear surface member 30 at the corner portion of the rear surface member 30. Therefore, for example, compared with a case where the support plate 50 is bonded to the rear surface member 30 at a portion other than the corner portion, the area of a portion surrounded by the bonded portion is increased. As a result, the effect of improving the stiffness of the rear surface member 30 is enhanced.

As a method of bonding the support plate 50 and the rear surface member 30 to each other, in addition to the method of inserting the protruding portion 58 into the mounting hole formed by the mounting rib 38, various methods such as screwing, welding, and bonding can be adopted. Materials of the support plate 50 and the rear surface member 30 can be freely selected, and any bonding method suitable for the materials can be selected.

Furthermore, as shown in FIG. 5, a reinforcing rib 56 is formed on the support plate 50. The protruding portion 58 is formed in the outer peripheral portion reinforcing rib 56C formed in a frame shape among the reinforcing ribs 56. The support plate 50 is fixed to the rear surface member 30 by the protruding portion 58. Therefore, the rear surface member 30 has a triple frame structure of the outer rib 32A, the inner rib 32B, and the outer peripheral portion reinforcing rib 56C in a state in which the rear surface member 30 is bonded to the support plate 50. As a result, the effect of suppressing the deformation of the rear surface member 30 is further enhanced.

In a portion surrounded by the outer peripheral portion reinforcing rib 56C in the support plate 50, the reinforcing ribs 56A and 56B and the support posts 52 and 54 are connected to each other. Therefore, compared with the configuration without the reinforcing ribs 56A and 56B and the support posts 52 and 54, the outer peripheral portion reinforcing rib 56C is less likely to be deformed. As a result, the effect of suppressing the deformation of the rear surface member 30 is further enhanced.

Since the support plate 50 and the rear surface member 30 are bonded to each other as described above, the rear surface member 30 is reinforced, and the support plate 50 is similarly reinforced. That is, in the support plate 50, the protruding portion 58 in the outer peripheral portion reinforcing rib 56C formed in the outer peripheral portion of the support plate 50 is fixed to the rear surface member 30. Therefore, the stiffness of the support plate 50 is higher than that in a configuration in which the support plate 50 is not fixed to the rear surface member 30.

The rear surface member 30 comprises the mounting rib 38 to which the protruding portion 58 of the support plate 50 is attached, the connection rib 36 to which the mounting rib 38 is connected, and the outer rib 32A and the inner rib 32B connected to each other by the connection rib 36. Therefore, the rear surface member 30 is stiffened by the frame-shaped outer rib 32A and inner rib 32B.

In the radiation detection device 10, as shown in FIG. 4, the intermittent portions 32BA and 32BB and the through holes 32AA and 32AB as opening portions, through which the battery 100 as an externally inserted member is inserted, are formed in the outer rib 32A and the inner rib 32B. The opening connection rib 36B is formed at both ends of the opening portions 30A and 30B in the rear surface member 30 formed as described above. Therefore, since the opening portions 30A and 30B are reinforced, the opening portions 30A and 30B are hardly deformed.

The mounting rib 38 is connected to the opening connection rib 36B, and the support plate 50 is bonded to the mounting hole formed by this mounting rib 38. Therefore, the opening portions 30A and 30B are reinforced. In addition, since the protection rib 56D is formed on the support plate 50, the battery 100 inserted through the opening portions 30A and 30B is protected.

The opening portions 30A and 30B are formed at the central portion of the rear surface member 30, that is, on the center lines CL1 and CL2. Therefore, compared with a case where the opening portion is formed in the vicinity of the corner portion of the rear surface member 30, the influence in a case where an impact is applied to the corner portion is hardly received. For this reason, the opening portions are hardly deformed.

The opening portions 30A and 30B are formed on two sides adjacent to each other in the rear surface member 30. Therefore, as shown in FIG. 7, interference between the battery 100 and the signal processing unit 62A and the gate line driver 62B on the control substrate 60, which are provided along the two adjacent sides of the support plate 50, is suppressed. In addition, interference between the battery 100 and the flexible cables 46A and 46B connected to the signal processing unit 62A and the gate line driver 62B is suppressed.

In the radiation detection device 10, as shown in FIGS. 2 and 3, the bottom plate 34 of the rear surface member 30 is fixed to the double frame 32 using a screw or the like. Therefore, by removing the screw, the signal processing unit 62A, the gate line driver 62B, the image memory 62C, the controller 62D, and the like on the control substrate 60 can be replaced or maintenance therefor can be performed. In addition, the double frame 32 and the bottom plate 34 can be integrally formed. In this case, the stiffness of the double frame 32 can be further improved.

In the radiation detection device 10, the double frame 32 in the rear surface member 30 is gradually raised from the bottom surface onto which the bottom plate 34 is fitted to the outer edge portion in the direction of the front surface member 20, and the raised portion is the outer rib 32A. Therefore, for example, in the case of inserting the radiation detection device 10 between the bed and the patient, a situation in which the outer rib 32A is caught on a sheet or clothes is suppressed. As a result, the workability is improved.

A packing (not shown) is disposed between the front surface member 20 and the surface of the outer rib 32A, which faces the front surface member 20, in the rear surface member 30, so that the internal space formed between the front surface member 20 and the rear surface member 30 is a watertight space. Therefore, it is possible to protect the support plate 50 formed of a MgLi alloy having lower corrosion resistance than a Mg alloy.

In the radiation detection device 10, a side, which is a side along the short side of the radiation detection device 10 (that is, a side along the Y direction) and on which the opening portion 30A is not formed, among the sides of the inner rib 32B is disposed such that the separation distance from the outer rib 32A is larger than those of the other sides. Therefore, compared with a case where the separation distance is the same as those of the other sides, the effect of suppressing deformation with respect to the impact along the X direction is enhanced.

In the radiation detection device 10, the opening portions 30A and 30B through which the battery 100 is inserted are formed on the side surface of the rear surface member 30. Therefore, for example, in a case where the radiation detection device 10 is used in a state in which the radiation detection device 10 is attached to the imaging table, the battery 100 and the imaging table are not easily caught with each other, so that the imaging table is easily ejected.

On the other hand, for example, in a case where an opening portion for installing the battery 100 is formed on the back surface of the rear surface member 30, the battery cover or the like may protrude from the back surface to be caught with the imaging table. In a case where the opening portion for the battery is provided on the back surface which often contacts various places, such as a work table and a bed, dust or the like is likely to clog a gap between the battery and the rear surface member 30.

In the radiation detection device 10, as shown in FIGS. 2 and 5, a plurality of tubular support posts 52 and 54 are formed in contact with the surface of the support plate 50 not facing the radiation detection panel 40, and the support posts 52 and 54 are disposed in contact with the bottom plate 34 of the housing 12. In addition, "in contact with" includes a state of being formed integrally with the support plate 50 as in the case of the support posts 52 and 54.

Here, the support plate 50 is formed of a MgLi alloy. The MgLi alloy has a smaller specific gravity than, for example, a Mg alloy or an aluminum alloy (Al alloy). For this reason, by using the MgLi alloy as the support plate 50, the weight can be reduced as compared with the Mg alloy or the like.

The MgLi alloy has a smaller Young's modulus and a lower stiffness than the Mg alloy, the Al alloy, and the like. In the present embodiment, in a case where the radiation detection device 10 is pressed from the outside at the time of use of the radiation detection device 10 and a load in the out-of-plane direction acts on the radiation detection panel 40, the load received by the support plate 50 is transmitted to the housing 12 by the support posts 52 and 54. Therefore, the support plate 50 is hardly deformed. In addition, by forming the support posts 52 and 54 in a tubular shape, both suppression of deformation of the support plate 50 and reduction in the weight of the support plate 50 can be realized.

In the radiation detection device 10, the support posts 52 and 54 are formed in a hexagonal shape, and the support posts 52 and 54 adjacent to each other are disposed such that the side 52A and the short side 54A face each other. In addition, the support posts 54 adjacent to each other are disposed such that the long sides 54B face each other.

Therefore, the supporting force of the support posts 52 and 54 can be increased. That is, in a case where the radiation detection device 10 is pressed from the outside at the time of use of the radiation detection device 10 and a load in the out-of-plane direction acts on a portion of the radiation detection panel 40 between the support posts 52 and 54, the load is transmitted to the support posts 52 and 54.

In this case, since the load is supported by the side 52A and the short side 54A, the internal stress generated in the support posts 52 and 54 is dispersed, for example, in the case of supporting the support posts 52 and 54 at the apex of the hexagonal shape. Therefore, the supporting force of the support posts 52 and 54 is increased.

In the radiation detection device 10, the support posts 52 and 54 are formed along a direction perpendicular to the in-plane direction, and the axial direction of each of support posts 52 and 54 is the out-of-plane direction of the support plate 50. Therefore, the supporting force against the external force from the direction perpendicular to the support plate 50 and the transmission plate 22 is high.

In the radiation detection device 10, the support posts 52 and 54 are molded integrally with the support plate 50. Therefore, the load received by the support plate 50 is easily transmitted to the support posts 52 and 54. In addition, for example, compared with a case where the support posts 52 and 54 and the support plate 50 are bonded to each other, the followability to the out-of-plane deformation of the support plate 50 is high, and the durability is high.

In the radiation detection device 10, the reinforcing ribs 56A and 56B in contact with the support plate 50 are bridged between the support posts 52, between the support posts 54, and between the support posts 52 and 54. Therefore, in a case where the load in the out-of-plane direction acts between the support posts 52, between the support posts 54, and between the support posts 52 and 54, the load is transmitted to the reinforcing ribs 56A and 56B and further transmitted to the support posts 52 and 54.

As described above, since the load is once transmitted to the reinforcing ribs 56A and 56B before the load is transmitted to the support posts 52 and 54, the reinforcing ribs 56A and 56B function as beam members to suppress the out-of-plane deformation of the support plate 50.

In the present embodiment, the gate line driver 62B and the signal processing unit 62A are disposed so as to be in direct contact with the support plate 50 without using a mount member, such as a resin. Therefore, since the heat emitted from the gate line driver 62B and the signal processing unit 62A is dissipated to the support plate 50, the durability of the gate line driver 62B and the signal processing unit 62A is improved. In addition, local heating of the inside of the radiation detection device 10 is suppressed.

Other Embodiments

Figure 8:
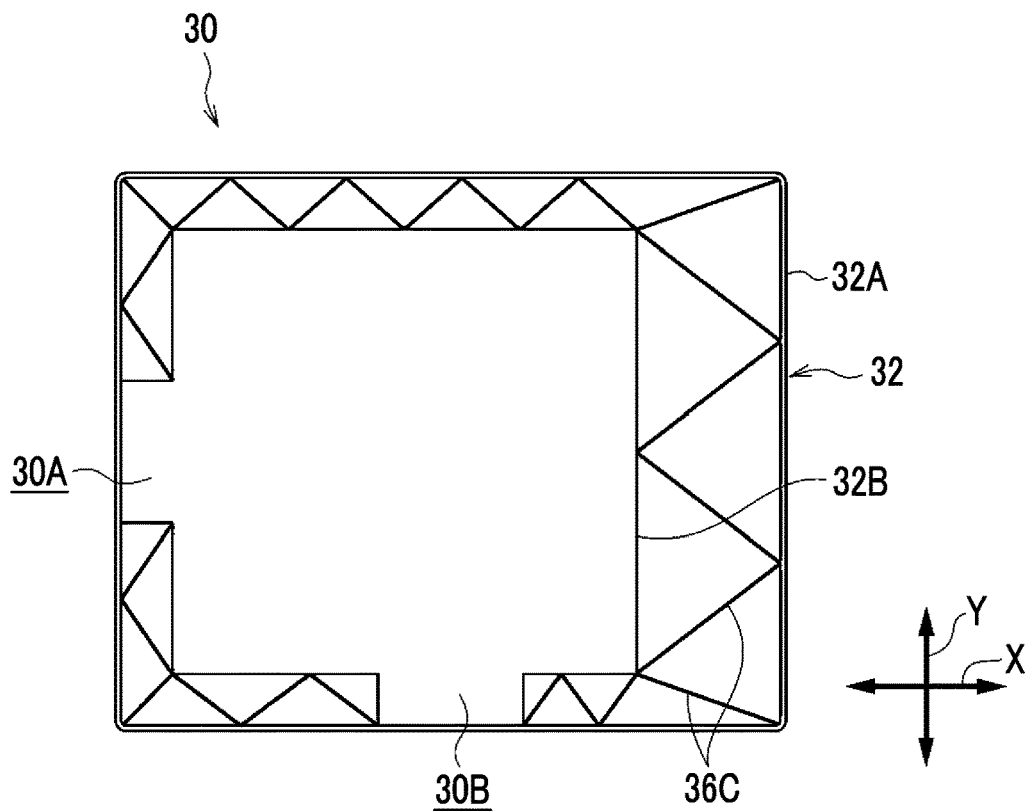
FIG. 8 is a front view showing a modification example in which a truss structure is formed by reinforcing ribs of the rear surface member in the radiation detection device according to the present embodiment.

In the above embodiment, as shown in FIG. 4, the connection rib 36 extends in a direction approximately perpendicular to the outer rib 32A and the inner rib 32B. However, the embodiment of the invention is not limited thereto. For example, as in the case of a connection rib 36C shown in FIG. 8, a connection rib may be provided so as to extend in a direction crossing the outer rib 32A and the inner rib 32B so that a triangle is formed by the connection rib 36C and the outer rib 32A or the inner rib 32B. In this case, since the outer rib 32A, the inner rib 32B, and the connection rib 36C form a truss structure, it is possible to increase the stiffness of the double frame 32.

In the above embodiment, the connection rib 36 is "bonded" to the outer rib 32A and the inner rib 32B. However, the embodiment of the invention is not limited thereto. For example, a gap may be provided between the connection rib 36 and the inner rib 32B. The size of the gap is preferably such that the gap is closed in a case where an external force is applied to the outer rib 32A to bring the connection rib 36 and the inner rib 32B into contact with each other. In this case, the external force can be transmitted to the inner rib 32B.

In a case where it is necessary to increase the gap between the connection rib 36 and the inner rib 32B, for example, the connection rib 36 is formed thick, so that the external force applied to the outer rib 32A is transmitted from the connection rib 36 to the rear surface side (back side of the sheet in FIG. 4) of the connection rib 36 in the double frame 32. By forming the gap in this manner, various wirings in the radiation detection panel 40 or the control substrate 60 can be disposed inside the double frame, that is, between the outer rib 32A and the inner rib 32B. This can improve the degree of freedom in wiring arrangement.

In addition, in order to improve the degree of freedom in wiring arrangement, at least one of the inner rib 32B and the connection rib 36 may be partially lowered or cut away to form a defect portion, and the wiring may be made to pass through the defect portion. Instead of or in addition to the defect portion, a through hole may be formed in the inner rib 32B and the connection rib 36, and the wiring may be made to pass through the through hole.

In the above embodiment, as shown in FIG. 4, the thickness H2 of the inner rib 32B is set to be smaller than the thickness H1 of the outer rib 32A. However, the embodiment of the invention is not limited thereto. For example, as in the case of an inner rib 32D shown in FIG. 9, the inner rib may have the same thickness as the outer rib 32A. In this case, the stiffness of the double frame 32 can be improved. Alternatively, the width H3 of the double frame 32 can be reduced while maintaining the stiffness of the double frame 32. By reducing the width H3 of the double frame 32, for example, the sizes of the support plate 50 and the radiation detection panel 40 can be increased to increase the detectable radiation dose.

Figure 9:
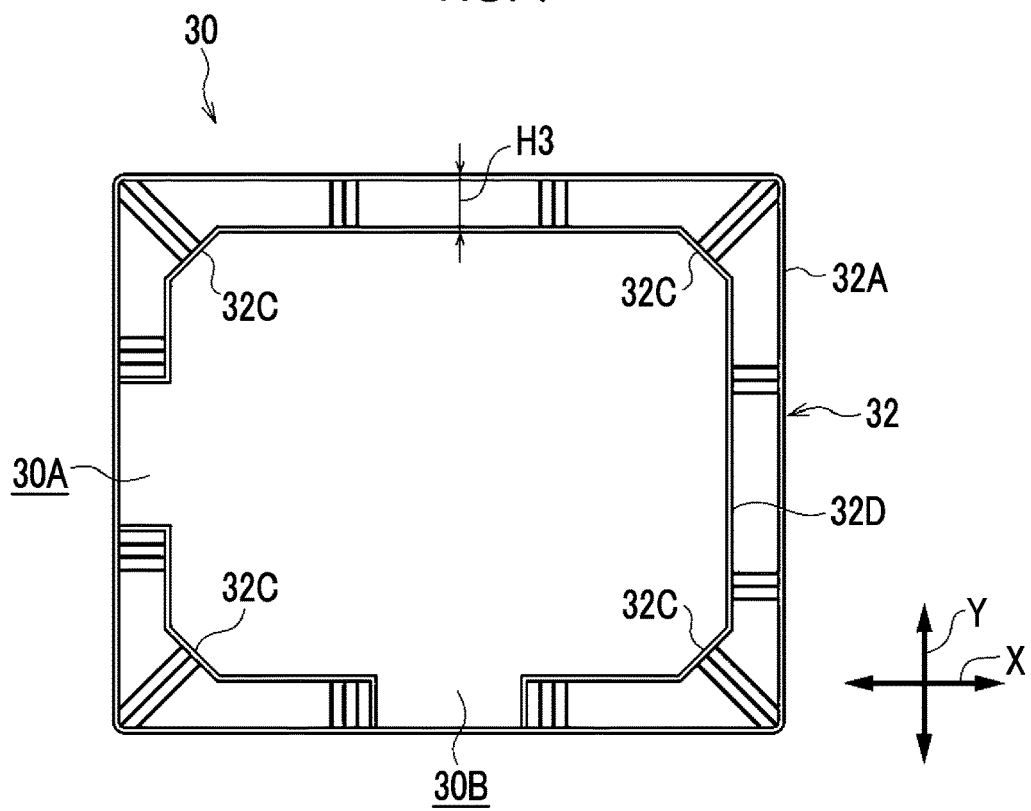
FIG. 9 is a front view showing a modification example in which an inner rib and an outer rib of the rear surface member in the radiation detection device according to the present embodiment are formed so as to have the same thickness.

In the above embodiment, as shown in FIG. 4, the inner rib 32B on the short side where the opening portion 30A is not formed is disposed such that the separation distance from the outer rib 32A is larger than that in the case of the inner rib 32B on the other sides. However, the embodiment of the invention is not limited thereto. For example, as shown in FIG. 9, the separation distance between the inner rib 32D and the outer rib 32A on the short side where the opening portion 30A is not formed may be the same as the separation distance between the inner rib 32D and the outer rib 32A on the other sides. In this case, it is preferable to provide the oblique portion 32C at both ends of the inner rib 32D on the short side where the opening portion 30A is not formed.

In the embodiment shown in FIG. 9, the thick inner rib 32D may be replaced with the thin inner rib 32B. Alternatively, the separation distance between the thick inner rib 32D and the outer rib 32A on the short side where the opening portion 30A is not formed may be larger than the separation distance between the inner rib 32D and the outer rib 32A on the other sides.

Figure 10:
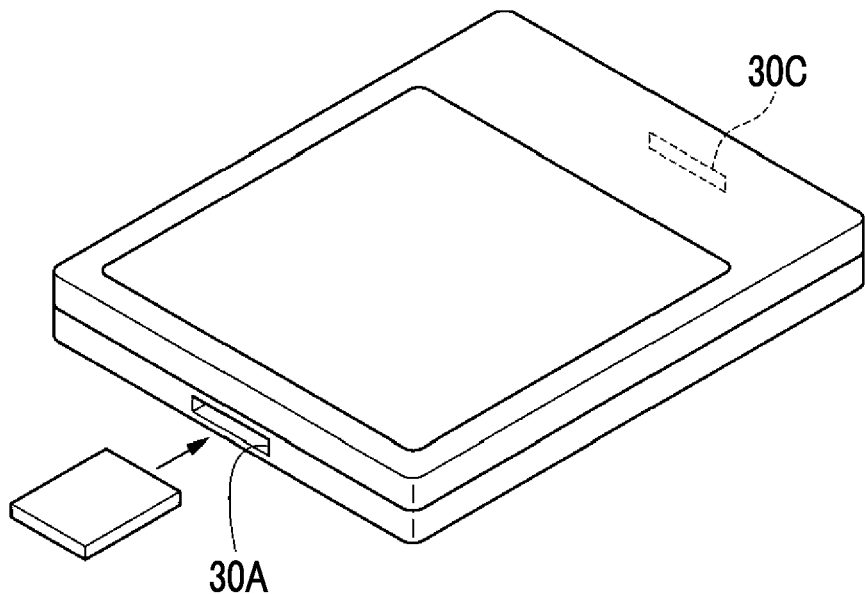
FIG. 10 is a perspective view showing a modification example in which an opening portion for battery insertion is provided only on the short side in the radiation detection device according to the present embodiment.

In the above embodiment, as shown in FIG. 1, the opening portions 30A and 30B through which the battery 100 is inserted are formed on the adjacent side surfaces of the rear surface member 30. However, the embodiment of the invention is not limited thereto. For example, as shown in FIG. 10, the opening portion 30A may be formed on only one short side of the rear surface member 30. Alternatively, the opening portions 30A and 30C may be formed on two short sides facing each other.

Figure 11:
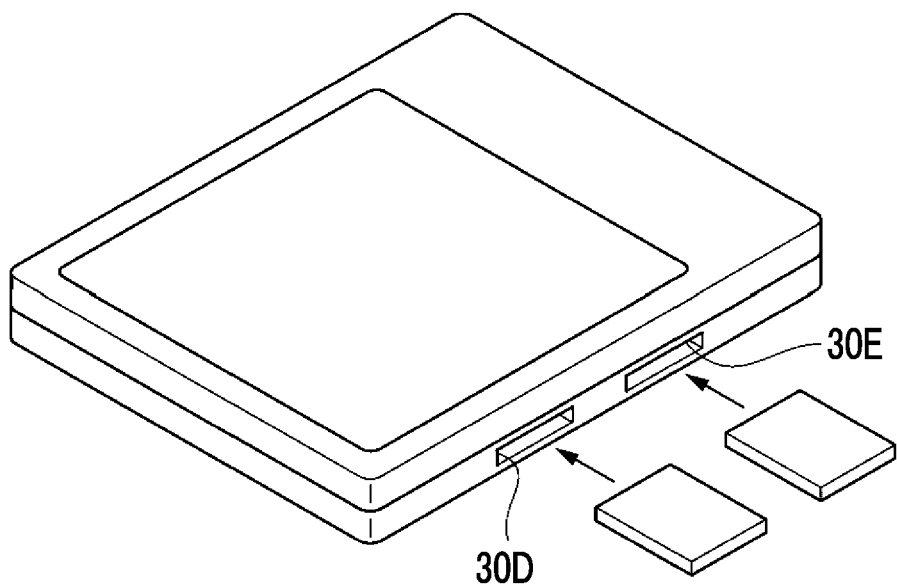
FIG. 11 is a perspective view showing a modification example in which two opening portions for battery insertion are provided on the same side surface in the radiation detection device according to the present embodiment.

Alternatively, as shown in FIG. 11, two opening portions 30D and 30E may be formed on only one long side of the rear surface member 30. Alternatively, although not shown, one opening portion may be provided on only one long side of the rear surface member 30.

Figure 12:
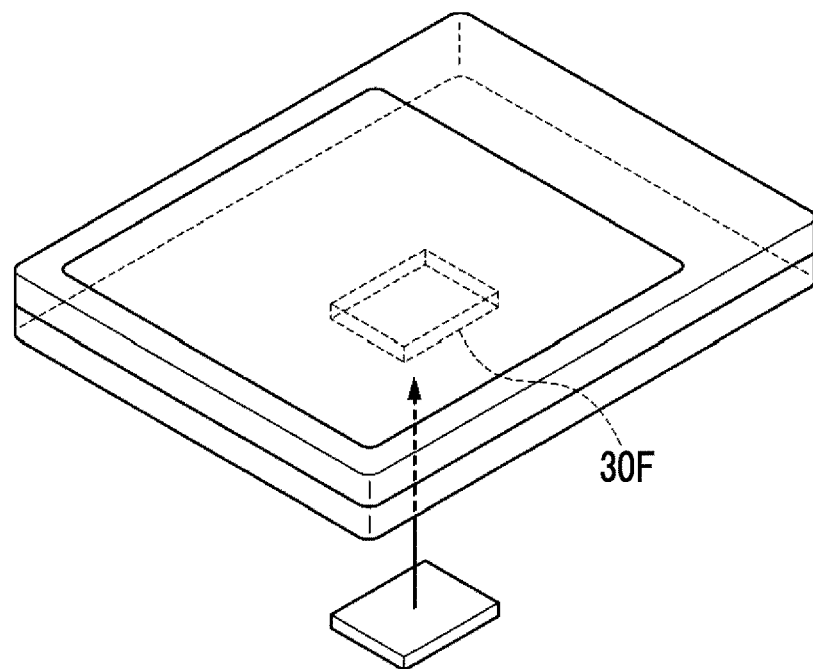
FIG. 12 is a perspective view showing a modification example in which an opening portion for battery insertion is provided on the back surface of the rear surface member in the radiation detection device according to the present embodiment.

In addition, as in the case of an opening portion 30F shown in FIG. 12, an opening portion may be provided not on the side surface of the rear surface member 30 but on the rear surface thereof. In the embodiment having two opening portions, one battery may be an externally inserted battery, and the other battery may be a built-in battery. The built-in battery comprises a terminal, and is charged by connecting a charging cable from the outside. As components inserted through the opening portion, not only the battery but also a memory card, a communication device, and the like can be appropriately adopted.

In the above embodiment, the outer rib 32A and the inner rib 32B are formed in a frame shape. However, the embodiment of the invention is not limited thereto. For example, by forming at least one of the outer rib 32A or the inner rib 32B only in the corner portion of the rear surface member 30, it is possible to efficiently protect the corner portion that is susceptible to collision and deformation.

Alternatively, the outer rib 32A and the inner rib 32B may be partially formed in a part of the side surface along the X and Y directions without being limited to the corner portion of the rear surface member 30. Since the stiffness of the part is also increased by partially forming the outer rib 32A and the inner rib 32B, the effect of protecting the radiation detection panel 40 can be obtained.

Figure 13:
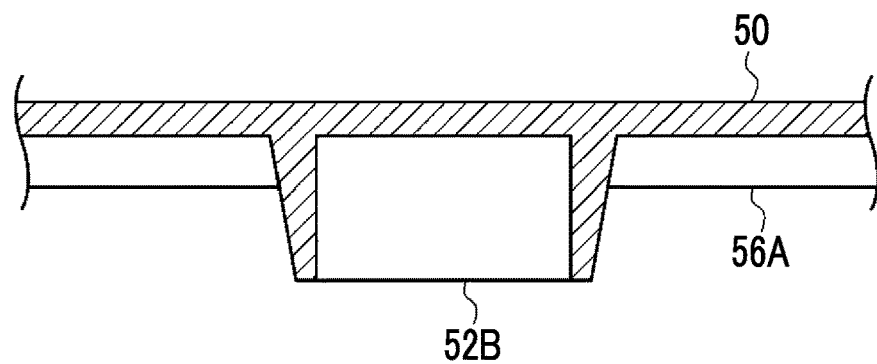
FIG. 13 is a cross-sectional view showing a modification example in which a support post formed on the support plate in the radiation detection device according to the present embodiment is formed such that the thickness of the support post gradually increases from a distal end portion thereof toward the support plate.

In the above embodiment, as shown in FIG. 2, the wall surface of the support post 52 is formed perpendicular to the support plate 50. However, the embodiment of the invention is not limited thereto. For example, as in the case of a support post 52B shown in FIG. 13, a support post may be formed such that the thickness of the support post gradually increases from the distal end of the support post 52B toward the support plate 50. In this manner, since the strength is improved compared with the support post 52 and the draft after molding is obtained, it is possible to enhance the manufacturing efficiency. The draft angle is preferably about 6° with respect to the normal direction of the support plate 50.

Figure 14:
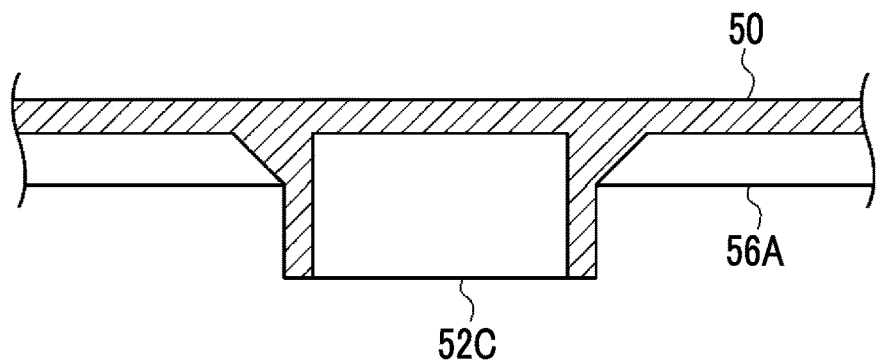
FIG. 14 is a cross-sectional view showing a modification example in which a support post formed on the support plate in the radiation detection device according to the present embodiment is formed such that the thickness of the support post gradually increases from a central portion in the axial direction toward the support plate.

Alternatively, as in the case of a support post 52C shown in FIG. 14, a support post may be formed such that the thickness of the support post gradually increases toward the support plate 50 from an intermediate portion in a height direction along the axial direction. In this manner, it is possible to reinforce the root portion of the support post 52C on which stress is easily concentrated while suppressing an increase in the weight of the entire support plate 50.

Figure 15:
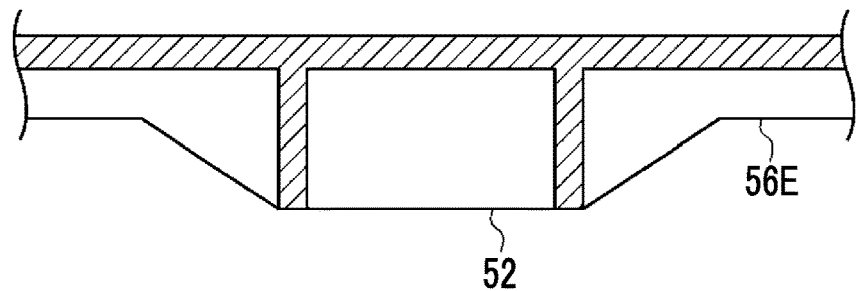
FIG. 15 is a cross-sectional view showing a modification example in which an end portion of a reinforcing rib formed on the support plate in the radiation detection device according to the present embodiment is formed such that the thickness of the end portion gradually increases toward the support plate.

In the above embodiment, as shown in FIG. 2, the thickness of the reinforcing rib 56A along the axial direction of the support post 52 is fixed. However, the embodiment of the invention is not limited thereto. For example, as in the case of a reinforcing rib 56E shown in FIG. 15, the thickness of a reinforcing rib along the axial direction of the support post 52 may be gradually increased at a place of connection with the support post 52. In this case, in a case where a load is input from the support plate 50 to the reinforcing rib 56E, the resistance against bending moment and shear force acting on the boundary between the reinforcing rib 56E and the support post 52 is increased. Therefore, the load can be efficiently transmitted to the support post 52.

The configuration in which the thickness is gradually increased along the axial direction of the support post 52 at the place of connection with the support post 52 as described above can also be applied to the reinforcing rib 56B.

Figure 16:
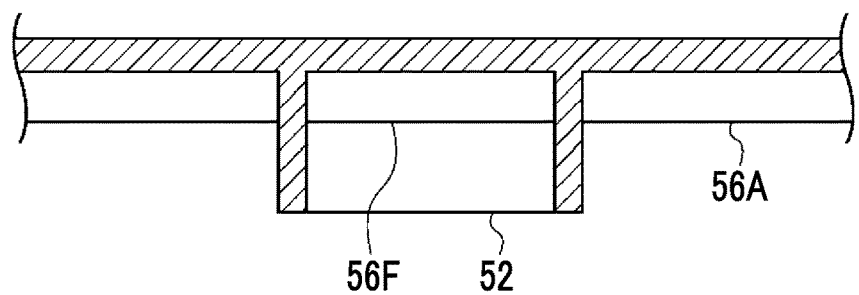
FIG. 16 is a cross-sectional view showing a modification example in which a reinforcing rib is formed inside the support post formed on the support plate in the radiation detection device according to the present embodiment.

In the above embodiment, as shown in FIG. 2, the inside of the tubular support post 52 is hollow. However, the embodiment of the invention is not limited thereto. For example, as shown in FIG. 16, an inner reinforcing rib 56F may be bridged between the inner walls of the support post 52. In this case, the buckling of the support post 52 can be suppressed.

In addition, as shown by the broken line in FIG. 5, the inner reinforcing rib 56F is preferably disposed on the extension of the reinforcing rib 56A. In this case, deformation of the support post 52 due to the load transmitted from the reinforcing rib 56A is suppressed.

In the above embodiment, the support post 52 is formed integrally with the support plate 50, and is formed in a tubular shape in which the axial direction is the out-of-plane direction (direction perpendicular to the in-plane direction) of the support plate 50. However, the embodiment of the invention is not limited thereto.

Figure 17:
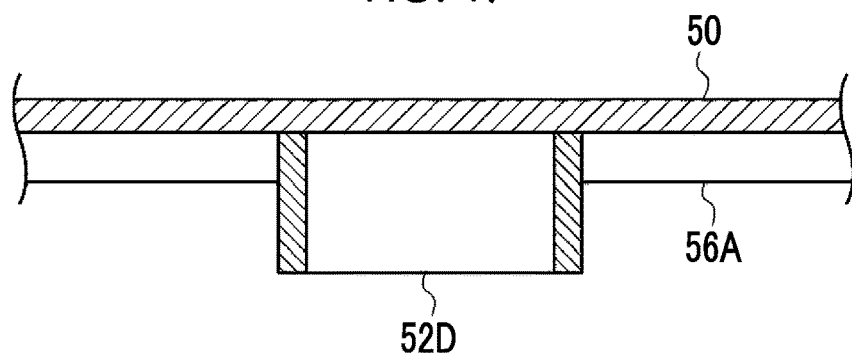
FIG. 17 is a cross-sectional view showing a modification example in which the support post and the support plate in the radiation detection device according to the present embodiment are formed as separate bodies.

As an example, as in the case of a support post 52D shown in FIG. 17, a support post and the support plate 50 may be provided as separate bodies. In this case, the reinforcing ribs 56A and 56B may be formed integrally with the support post 52D or may be formed as separate bodies. In a case where the reinforcing ribs 56A and 56B and the support post 52D are separate bodies, the reinforcing ribs 56A and 56B and the support post 52D are fixed by bonding. It is preferable that the support post 52D and the reinforcing ribs 56A and 56B are bonded to the support plate 50.

Figure 18:
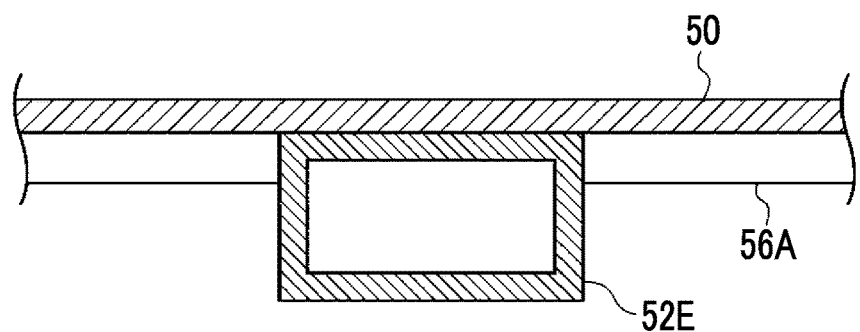
FIG. 18 is a cross-sectional view showing a modification example in which the support post and the support plate in the radiation detection device according to the present embodiment are formed as separate bodies and the axial direction of the support post is a direction along the in-plane direction of the support plate.

As another example, as in the case of a support post 52E shown in FIG. 18, a support post may be formed such that the axial direction of the support post follows the in-plane direction of the support plate 50.

Figure 19:
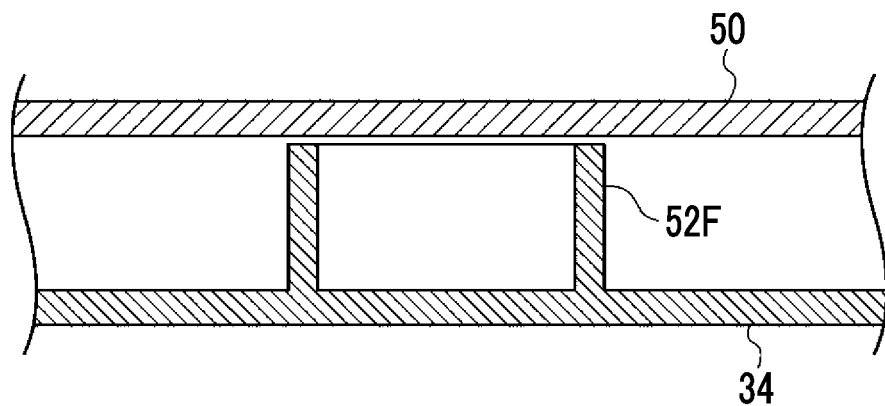
FIG. 19 is a cross-sectional view showing a modification example in which the support post is formed integrally with a bottom plate of the rear surface member in the radiation detection device according to the present embodiment.

As still another example, as in the case of a support post 52F shown in FIG. 19, a support post may be formed integrally with the bottom plate 34 of the rear surface member 30.

Also by the support posts 52D, 52E, and 52F, in a case where a load in the out-of-plane direction acts on the transmission plate 22 and the radiation detection panel 40, it is possible to stand the load. The configurations of the support posts 52D, 52E, and 52F can also be applied to the support post 54 shown in FIG. 5.

In the case of providing the support post and the support plate 50 as separate bodies, the support post can be formed of various materials. As the support post, metal-based materials, such as an Al alloy and a Mg alloy, can be used as an example.

As another example, it is possible to use resin materials, such as acrylonitrile butadiene styrene (ABS) resin, polycarbonate (PC) resin, modified-polyphenyleneether (PPE) resin, polyethylene (PE) resin, high density polyethylene (HDPE) resin, polypropylene (PP) resin, polyoxymethylene (POM) resin, liquid crystal polymer (LCP) resin, and polyetheretherketone (PEEK) resin.

As still another example, it is possible to use composite resin materials (reinforced plastics) reinforced by adding glass fiber, cellulose nanofiber, talc (calcium-based reinforcing material), magnesium fiber, and the like to the resin materials. As still another example, a carbon material, fiber-reinforced plastics (FRP), and the like can be used.

Figure 20:
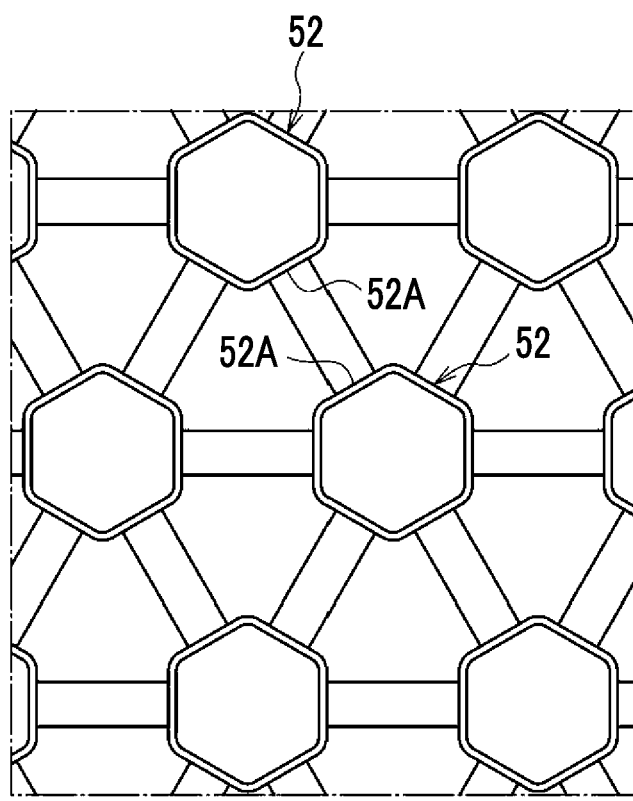
FIG. 20 is an enlarged plan view showing a modification example in which the support posts in the radiation detection device according to the present embodiment are formed as only support posts having the same shape.

In the above embodiment, the two support posts 52 and 54 having different shapes are disposed on the support plate 50. However, the embodiment of the invention is not limited thereto. For example, as shown in FIG. 20, only the support post 52 having an approximately regular hexagonal shape may be used. In such a case, it is preferable that the sides 52A of the support posts 52 adjacent to each other are disposed so as to face each other.

Figure 21:
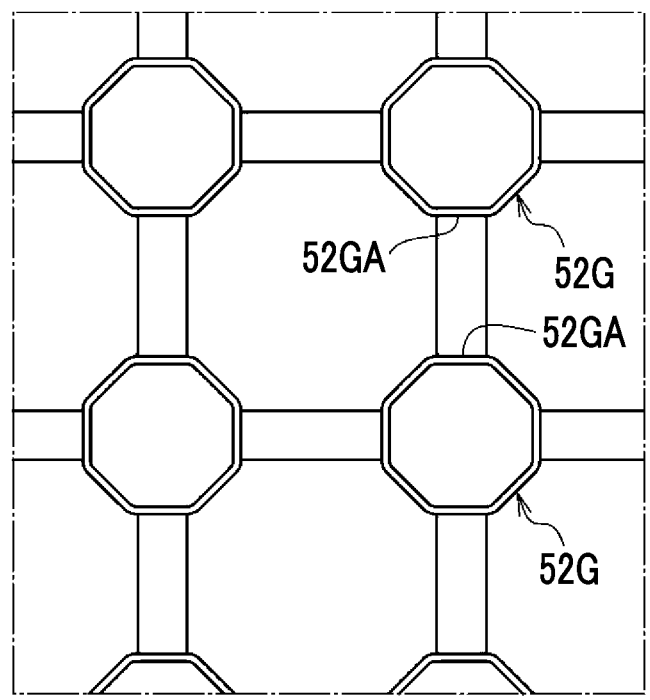
FIG. 21 is an enlarged plan view showing a modification example in which the support posts in the radiation detection device according to the present embodiment are formed in an octagonal shape.

In the above embodiment, the support posts 52 and 54 are formed in a hexagonal shape. However, the embodiment of the invention is not limited thereto. For example, as in a support post 52G shown in FIG. 21, a support post may have an octagonal shape. Also in such a case, it is preferable that sides 52GA of the support posts 52G adjacent to each other are disposed so as to face each other.

What is claimed is:

1. A radiation detection device, comprising:
   a front surface member;
   a rear surface member that is assembled with the front surface member and that comprises an outer rib formed along an outer edge and an inner rib formed along the outer rib inside the outer rib; and
   a radiation detection panel that is disposed between the front surface member and the rear surface member and detects radiation incident from the front surface member side.

2. The radiation detection device according to claim 1, wherein the outer rib and the inner rib are formed in a frame shape.

3. The radiation detection device according to claim 1, wherein the outer rib has a portion formed thicker than the inner rib.

4. The radiation detection device according to claim 1, wherein the outer rib and the inner rib are connected to each other by a connection rib.

5. The radiation detection device according to claim 4, wherein at least a part of the connection rib is a corner portion connection rib extending from a corner portion of the outer rib to the inner rib, and
   the inner rib is disposed perpendicular to the corner portion connection rib.

6. The radiation detection device according to claim 4, wherein the outer rib, the inner rib, and the connection rib form a truss structure.

7. The radiation detection device according to claim 1, further comprising:
   a support plate that supports the radiation detection panel, wherein the support plate is bonded to the rear surface member.

8. The radiation detection device according to claim 7, wherein the support plate is bonded to a corner portion of the rear surface member.

9. The radiation detection device according to claim 7, wherein a reinforcing rib is formed on the support plate, and
   the reinforcing rib and the rear surface member are bonded to each other.

10. The radiation detection device according to claim 7, wherein an opening portion through which an externally inserted member is inserted is formed on side surfaces of the outer rib and the inner rib, and
    an opening connection rib is formed at both ends of the opening portion.

11. The radiation detection device according to claim 10, wherein the opening portion is formed in a central portion of the rear surface member.

12. The radiation detection device according to claim 10, wherein the opening portion is formed on two sides adjacent to each other in the rear surface member.

13. The radiation detection device according to claim 10, wherein a protection rib surrounding the externally inserted member inserted through the opening portion is formed on the support plate.

* * * * *